United States Patent [19]
Fiala

[11] Patent Number: 5,410,375
[45] Date of Patent: Apr. 25, 1995

[54] MULTIFOCAL BIREFRIGENT LENS WITH ADJUSTED BIREFRINGENCE

[76] Inventor: Werner J. Fiala, Staudgasse 88/11, A-1180 Vienna, Austria

[21] Appl. No.: 927,525

[22] PCT Filed: Mar. 8, 1991

[86] PCT No.: PCT/AT91/00042

§ 371 Date: Oct. 22, 1992

§ 102(e) Date: Oct. 22, 1992

[87] PCT Pub. No.: WO91/14189

PCT Pub. Date: Sep. 19, 1991

[30] Foreign Application Priority Data

Mar. 15, 1990 [AU] Australia .................. 619/90

[51] Int. Cl.⁶ .................. G02C 7/06; G02C 7/04; G02B 5/30; A61F 2/16
[52] U.S. Cl. .................. 351/168; 351/161; 351/172; 359/494; 359/495; 359/497; 623/6
[58] Field of Search .................. 351/168–172, 351/160 R, 160 H, 161, 162; 359/494, 495, 497; 623/6

[56] References Cited

U.S. PATENT DOCUMENTS

| | | | |
|---|---|---|---|
| 3,391,053 | 7/1968 | Kolb | 161/185 |
| 4,227,950 | 10/1980 | Spycher | 156/85 |
| 4,679,918 | 7/1987 | Ace | 351/163 |
| 4,793,703 | 12/1988 | Fretz, Jr. | 351/163 |
| 5,064,712 | 11/1991 | Fretz, Jr. | 428/212 |
| 5,073,021 | 12/1991 | Marron | 351/168 |
| 5,116,684 | 5/1992 | Fretz, Jr. et al. | 428/417 |
| 5,142,411 | 8/1992 | Fiala | 351/168 |

FOREIGN PATENT DOCUMENTS

0388719 8/1990 European Pat. Off. .
0477658 11/1991 European Pat. Off. .

*Primary Examiner*—Scott J. Sugarman
*Attorney, Agent, or Firm*—Hoffmann & Baron

[57] ABSTRACT

Described is a multifocal bi-refrigent lens system with at least two different refractive powers which are necessary for optical applications. All lenses in the lens system are made from a bi-refrigent polymer whose bi-refringence is adjusted by stretching so that a single lens made of this polymer has these two different refractive powders.

18 Claims, 2 Drawing Sheets

MULTIFOCAL BIREFRINGENT LENS WITH ADJUSTED BIREFRINGENCE

The invention relates to a bifocal lens means made of birefringent material the birefringent material being a polymer which has been made birefringent by an orienting process by stretching under defined conditions, the material exhibiting an ordinary refractive index $n_O$ and an extraordinary refractive index $n_e$ after the orienting process, the lens means exhibiting two powers $D_{min}$, $D_{max}$ necessary for a specific optical application, the powers being measured for the lens system being immersed in a medium of refractive index $n_m$.

Birefringent multifocal lens systems are disclosed in EP 0 308 705 A2 or in U.S. Pat. No. 4,981,342. These lens systems comprise birefringent and/or isotropic lens components or single lenses, such that at least two powers of the lens system can be given predetermined values in independence of the material properties of the lens components of the lens system. It is shown that a lens system has to comprise at least one birefringent lens component and at least one isotropic of another birefringent lens component in order to provide at least two arbitrarily selected powers. It was further shown that at least two birefringent lens components and at least one isotropic or another birefringent lens component are required in order to provide at least three arbitrarily selected powers etc. In general, it was shown that in a lens system consisting of M birefringent lens components the number $N_{free}$ of independently selectable powers is $N_{free}=M$. It is further shown in the above European patent application and U.S. Pat. No. (equation 23) that at least another birefringent or isotropic lens component has to be added to the M birefringent lens components in order to provide $N_{free}=M+1$ independently selectable powers.

It is an object of the invention to provide structurally simple ophthalmic lens means which exhibits two different powers $D_{max}$, $D_{min}$ which may be preselected in complete independence of one another.

According to the invention this is achieved in that the lens means is a birefringent single lens and in that the birefringent of the birefringent material is so adjusted by means of the orienting process that for the value of the birefringence $\delta n = n_e - n_O$ either equation $$\delta n = (n_o - n_m)\left(\frac{D_{max}}{D_{min}} - 1\right)$$

or equation $$\delta n = (n_o - n_m)\left(\frac{D_{min}}{D_{max}} - 1\right)$$

is satisfied.

A specific embodiment of the invention is a simultaneous vision bifocal intraocular ophthalmic lens being immersed in a medium, which exhibits at least two deliberately preselectable or necessary power.

Figure 1:
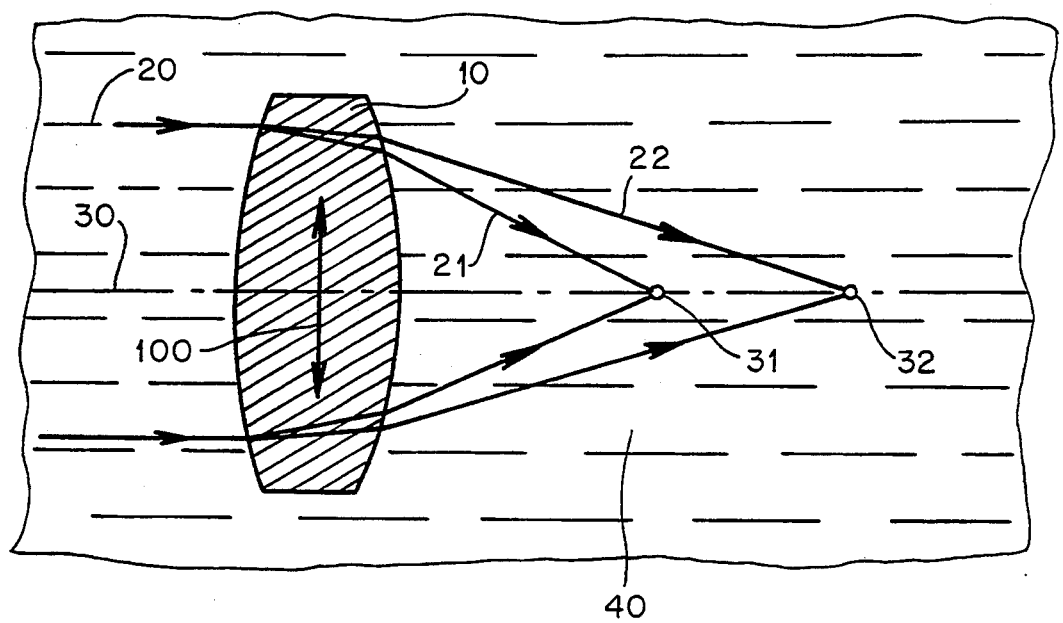
FIG. 1 is a single birefringent lens 10 according to this invention being made of a birefringent material the birefringence $\delta n$ of which is given by $$\delta n = (n_o - n_m)\left(\frac{D_{max}}{D_{min}} - 1\right)$$

where $D_{max}$ and $D_{min}$ are just the powers necessary for a optical application. By choosing this birefringence it is achieved that the single lens exhibits the two desired, i.e. preselected powers $D_{max}$ and $D_{min}$ when the lens is immersed in a medium 40 of refractive index $n_m$; the crystal optic axis 100 of lens 10 is perpendicular with the lens axis 30; light rays 20 incident in parallel with lens axis 30 are refracted by the lens 10 such that resultant light rays 21 and 22 are produced; rays 21 are focussed to focal point 31, rays 22 are focussed to focal point 32; focal point 31 corresponds to the maximum power $D_{max}$ of lens 10, focal point 32 corresponds to the minimum power $D_{min}$ of lens 10.

Figure 2:
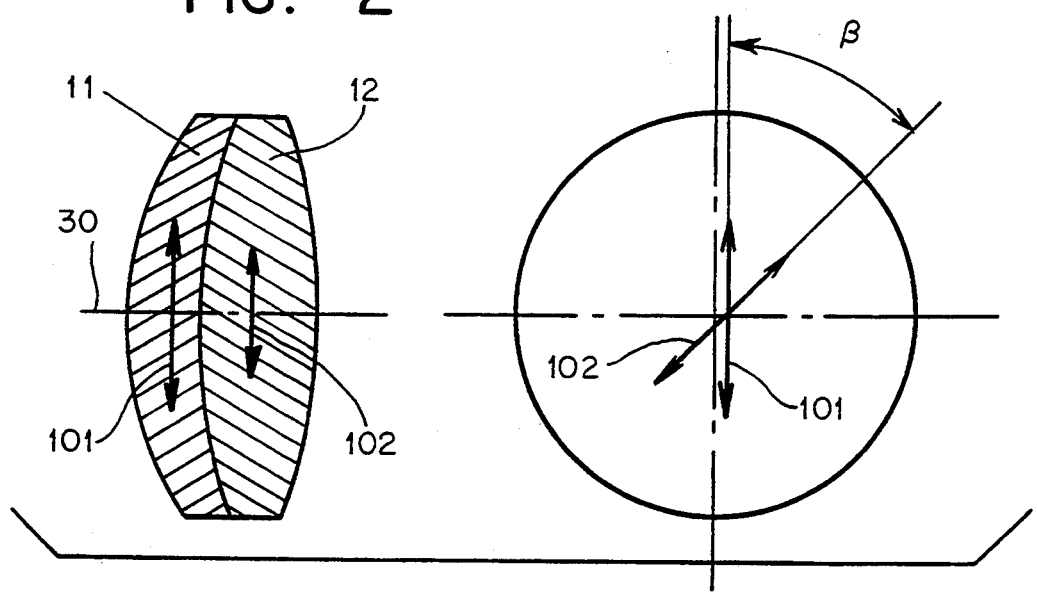

FIG. 2 is a birefringent lens system according to this invention; birefringent lenses 11 and 12 are fabricated from the same birefringent lens material; crystal optic axis 101 of lens 11 and crystal optic axis 102 of lens 12 are both perpendicular to axis 30 of both lenses 11 and 12; the angle between crystal optic axis 101 and crystal optic axis 102 is $\beta$. conditions, the material exhibiting an ordinary refractive index $n_o$ and an extraordinary refractive index $n_e$ after the orienting process, characterized in that the birefringence of the birefringent material is so adjusted by means of the orienting process that for the value of the birefringence $\delta n = n_e - n_o$ either equation $$\delta n = (n_o - n_m)\left(\frac{D_{max}}{D_{min}} - 1\right)$$

or equation $$\delta n = (n_o - n_m)\left(\frac{D_{min}}{D_{max}} - 1\right)$$

is satisfied, where $D_{max}$ and $D_{min}$ are two powers necessary for a specific optical application, the powers being measured for the lens system being immersed in a medium of refractive index $n_m$.

BRIEF DESCRIPTION OF THE DRAWINGS

FIG. 1 is a single birefringent lens 10 according to this invention being made of a birefringent material the birefringence $\delta n$ of which is given by $$\delta n = (n_o - n_m)\left(\frac{D_{max}}{D_{min}} - 1\right)$$

where $D_{max}$ and $D_{min}$ are just the powers necessary for a optical application. By choosing this birefringence it is achieved that the single lens exhibits the two desired, i.e. preselected powers $D_{max}$ and $D_{min}$ when the lens is immersed in a medium 40 of refractive index $n_m$; the crystal optic axis 100 of lens 10 is perpendicular with the lens axis 30; light rays 20 incident in parallel with lens axis 30 are refracted by the lens 10 such that resultant light rays 21 and 22 are produced; rays 21 are focussed to focal point 31, rays 22 are focussed to focal point 32; focal point 31 corresponds to the maximum power $D_{max}$ of lens 10, focal point 32 corresponds to the minimum power $D_{min}$ of lens 10.

FIG. 2 is a birefringent lens system according to this invention; birefringent lenses 11 and 12 are fabricated from the same birefringent lens material; crystal optic axis 101 of lens 11 and crystal optic axis 102 of lens 12 are both perpendicular to axis 30 of both lenses 11 and 12; the angle between crystal optic axis 101 and crystal optic axis 102 is $\beta$.

Figure 3:
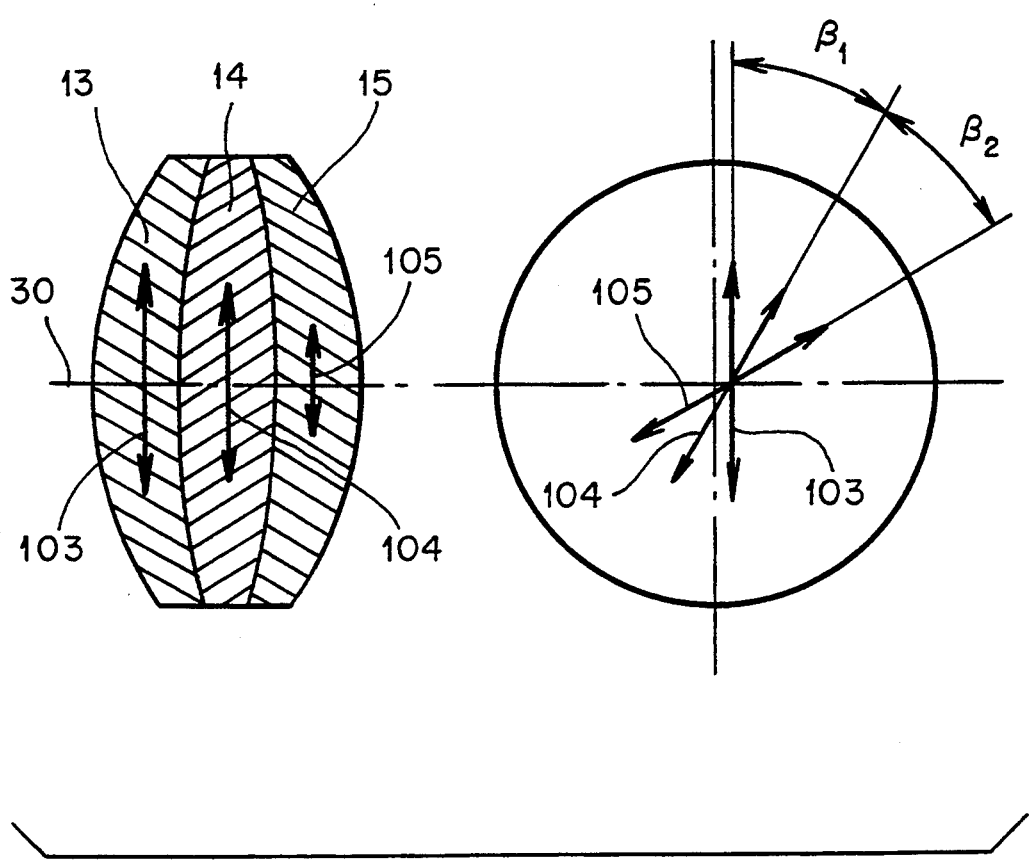

FIG. 3 is another birefringent lens system according to this invention; birefringent lenses 13,14 and 15 are fabricated from the same birefringent lens material; crystal optic axes 103, 104 and 105 of lenses 13,14 and 15, respectively, are all perpendicular with common axis 30 of lenses 13,14 and 15; the angle between crystal optic axes 103 and 104 is $\beta_1$ the angle between crystal optic axes 104 and 105 is $\beta_2$.

DESCRIPTION OF THE PREFERRED EMBODIMENTS

A. SINGLE BIFOCAL BIREFRINGENT LENS

As an approximation, the two powers $D_o$ and $D_e$ of a birefringent lens, said powers being measured in air, are given by $$D_o = (n_o - 1)S \quad (1)$$

$$D_o = (n_o - 1)S \quad (1)$$

and $$D_e = (n_e - 1)S \quad (2)$$

where $D_O$ is the power associated with the ordinary rays, $D_e$ the power of the extraordinary rays, $n_o$ is the ordinary index of refraction, $n_e$ is the extraordinary index of refraction, and S is the shape factor of the lens. The shape factor S (see e.g.: J. Strong: "Concepts of Classical Optics", p. 319, W. H. Freeman and Company, 1958) is a function of the geometrial parameters of the lens. For the sake of simplicity, it can be said that the shape factor S is approximately given by:

$$S = 1/R_F - 1/R_B \quad (i)$$

wherein $R_F$ is the front radius of the lens, and $R_B$ is the back radius of the lens; the radii are considered positive if the associated lens surfaces are convex for incident light; they are negative, if the associated lens surface is concave for incident light. If this lens is immersed in a medium of refractive index $n_m$, the powers $D_{o,m}$ and $D_{e,m}$ of the lens associated with the ordinary index and extraordinary index, respectively, are given by:

$$D_{o,m} = (n_o - n_m)S \quad (3)$$

and $$D_{e,m} = (n_e - n_m)S \quad (4)$$

wherein $D_{o,m}$ and $D_{e,m}$ are the powers of the lens immersed in the medium.

It can be deduced immediately from equations 1 through 4 that the power difference of a birefringent lens is independent of the index of refraction of the medium in which the lens is immersed, i.e.:

$$D_e - D_o = D_{e,m} - D_{o,m} = (n_e - n_o)S \quad (5)$$

If a birefringent lens is to exhibit the two powers $D_{o,m}$ and $D_{e,m}$, when immersed in a medium of refractive index $n_m$, which powers are necessary for a specific optical application, the two indices of the lens must satisfy the condition $$n_e = n_m + \frac{D_{e,m}}{D_{o,m}} (n_o - n_m) \quad (6)$$

If $D_{o,m}$ is the larger power called $D_{max}$ and $D_{e,m}$ is the smaller power called $D_{min}$ of both powers, equation 6 will lead to the following relation:

$$n_e - n_o = (n_o - n_m)\left(\frac{D_{max}}{D_{min}} - 1\right) \quad (6.1)$$

If on the other hand $D_{e,m}$ is the lager power called $D_{max}$ and $D_{o,m}$ is the smaller power called $D_{min}$ of both powers, equation 6 will lead to the following relation:

$$n_e - n_o = (n_o - n_m)\left(\frac{D_{min}}{D_{max}} - 1\right) \quad (6.2)$$

In general, it is not possible to satisfy equation (6) for any two desired, i.e. preselectable, powers $D_{o,m}$ and $D_{e,m}$ and for any immersion medium of given refractive index $n_m$ on the bais of a birefringent lens material which exhibits the given indices $n_o$ and $n_e$. For this reason EP 0 308 705 A2 and U.S. Pat. No. 4,981,342 provide at least two lens components in a birefringent lens system in order to provide two powers which are selectable in complete independence of one another.

But, as shown in the following, it is possible to satisfy equation 6, if the birefringent lens is fabricated from a lens material which is rendered birefringent by an orienting process such as stretching, and if different degrees of orientation, accompanied with different stretching ratios, are accompanied with different amounts of birefringence $\delta n = (n_e - n_o)$.

It is known from e.g. R. Weeger et al, *Colloid Polym Sci* 266:692–700 (1988), or J. A. Slee et al, *J. Polym. Sci. Polym. Phys.* Vol. 27, 71–80 (1989) that the birefringence induced in polymeric slabs by streching increases in a monotonous fashion with the draw ratio, assuming that all other parameters are kept constant. The induced birefringence depends also on many other parameters, e.g. temperature at drawing, drawing velocity, conditions for annealing and others. Most oriented polymers can be considered as an assembly of thin cylindrical rods. According to Max Born and Emil Wolf: *Principles of Optic*, Pergamon Press 6th Ed. p. 707 such media are positively birefringent, i.e. they exhibit two refractive indices with $n_e > n_o$.

If a polymeric sample exhibits an isotropic index $n_{iso}$ in its unstretched state, then, after stretching, the ordinary index $n_o$ of the sample will usually be smaller and the extraordinary index $n_e$ will be larger than the isotropix index $n_{iso}$. This behaviour—evidenced from stretching experiments—can be expressed by the empirical relation:

$$(n_e - n_{iso}) : (n_{iso} - n_o) = k \quad (7)$$

where k is typically 1 to 3. Combining the last three equations and solving for $(n_e - n_o)$ results in:

$$\delta n = (n_e - n_o) = (1 + k) \frac{(D_{e,m} - D_{o,m})(n_{iso} - n_m)}{(D_{e,m} - D_{o,m}) + (1 + k)D_{o,m}} \quad (8)$$

In the case of e.g. an intraocular lens the power difference $D_{e,m} - D_{o,m}$ is small in comparison with the powers $D_{e,m}$ or $D_{o,m}$, i.e.

$$D_{e,m} - D_{o,m} << D_{o,m}(1+k) \quad (9)$$

As a consequence, the required birefringence $n_e - n_o$ of an intraocular lens which should exhibit the two powers $D_{e,m}$ and $D_{o,m}$ is in the order of magnitude:

$$\delta n = (n_e - n_o) \leq \left(\frac{D_{e,m}}{D_{o,m}} - 1\right)(n_{iso} - n_m)$$

In the case of an intraocular lens typical values for the required powers are: $D_{min} = D_{o,m} = 20$ diopters and $D_{max} = D_{e,m} = 23$ diopters. It follows from equation 8 that the required birefringence is of the order of magnitude of 0.02 to 0.04 for stretched polymers which exhibit an isotropic refractive index of 1.5 to 1.6; higher isotropic indices require higher birefringences. J. A. Slee, Supra, reports birefringences between 0.011 and 0.138 induced in polyethyleneterephthalate (PET) by uniaxial stretching at various conditions and stretching ratios. Since the isotropic refractive indec of PET is appr. 1.58, it is evident that the required "adjusted" birefringence can be induced in slabs of PET e.g. by uniaxial stretching.

Various samples of appr. 2 to 4 mm thick polymeric slabs were stretched at various temperatures and to various stretching ratios. A few examples are given:

| Material | Birefringence |
| --- | --- |
| Polycarbonate | 0.01–0.05 |
| Polysulphone | 0.02–0.06 |
| Polyethersulphone | 0.01–0.08 |
| Polystyrene | 0.01–0.03 |
| Polyestercarbonate | 0.02–0.035 |

By way of specific example, polycarbonate was stretched to approximately twice of its original length at a temperature of approximately 135 degrees C. The indices—measured on a refractometer in polarized light—were found to be: $n_o = 1.57$ and $n_e = 1.606$. A biconvex lens of front radius 36 mm and back radius $-18$ mm, and centre thickness of 0.9 mm exhibited the two powers 20.2 and 23.3 dioptres measured in saline. The grid pattern could be clearly resolved for both powers on the focimeter. Slight deviations from the calculated theoretical powers are most probably due to inexact measurement of refractive indices. The sample lens is shown schematically in FIG. 1.

As can be appreciated from the aforesaid, it is possible to produce bifocal intraocular lenses for various power combinations by using lens materials of various birefringence. It is particularly advantageous that different birefringences can be induced in samples of identical chemical composition by appropriate variation of stretching conditions. Because of this, bio-compatibility tests have to be carried out for only one material, and also lathing techniques have to be established for one material only. Lens lathing techniques are practically identical with techniques applied in monofocal lens lathing, since at the required low birefringences mechanical anisotropy is not high, and the lens shape of the birefringent bifocal lens is that of a monofocal lens, i.e. it exhibits two smooth lens surfaces.

The advantages of multifocal lenses of the birefringent type, e.g. optimum intensity distribution, absence of intensity loss (in e.g. higher orders) independence of power values and intensity distribution of lens aperture, low chromatic abberation in both powers etc. are mentioned in EP 0 308 705 A2 and U.S. Pat. No. 4,981,342. It is well understood that these advantages apply also for the birefringent lens according to the present invention.

B. MULTIFOCAL LENS SYSTEMS WITH MORE THAN TWO POWERS

A birefringent lens according to this invention can be cut according to FIGS. 2 or 3, and then the partial lenses can be rotated about the common (symmetry) axis of said partial lenses such that the individual crystal optic axes exhibit deliberate angles one to the other (FIG. 2) or one to the others (FIG. 3). Then the lens system according to FIG. 2 can be made tri—or quadrafocal, the lens system according to FIG. 3 can be made tri-, quadra-, penta-, hexa-, hepta- or octafocal. In addition to the maximum and minimum powers $D_{min}$ and $D_{max}$ which determine the necessary birefringence according to equation 6.1 and 6.2, one additional power within the minimum and maximum values can be given an arbitrary value in the case of lens system according to FIG. 2. Two additional powers between $D_{min}$ and $D_{max}$ may be preselected in the case of a lens system according to FIG. 3. In general, the number $N_{free}$ of arbitrarily preselectable powers is therefore $$N_{free} = M + 1$$

wherein M is the number of birefringent lenses of the lens system. By comparison, lens system according to EP 0 308 795 A2 or U.S. Pat. No. 4,981,342 exhibit one arbitrarily selectable power less.

In lens system according to EP 0 308 705 A2 or U.S. Pat. No. 4,981,342, the maximum and minimum of available powers are provided by e-o-rays or o-e-rays in the case of a lens system comprising two birefringent lens components fabricated from the same birefringent lens medium. By contrast, due to the choice of birefringence according to Equation 6, the maximum and minimum powers of the present lens systems are provided by rays which are either ordinary or extraordinary rays in all of the present lenses, i.e. by o-o-rays or e-e-rays.

The general relations which govern the powers and the associated intensities of multifocal lens systems according to this invention are now presented; discussed is the case of a lens system fabricated from a positively birefringent polymeric lens medium.

If a lens system according to this invention is to provide the minimum power $D_{min}$ and a maximum power $D_{max}$, equations 6.1 and 6.2 determine the necessary or adjusted indices $n_o$ and $n_e$. With these indices $n_o$ and $n_e$ and the refractive index $n_m$ of the medium in which the lens is immersed (including, of course, the case $n_m = 1$) the shape factor S of the system is given by:

$$S = \frac{D_{o,m}}{n_o - n_m} = \frac{D_{e,m}}{n_e - n_m} \quad (11)$$

In the case of a lens system according to FIG. 2 the two lens components 101 and 102 can be given lens shape factors $S_1$ and $S_2$ with:

$$S_1 + S_2 = S \quad (12)$$

The four powers available from such a lens system are then given by:

$$(n_o - n_m)S_1 + (n_o - n_m)S_2 = D(oo) = D_{o,m} \quad (13A)$$

$$(n_e - n_m)S_1 + (n_o - n_m)S_2 = D(eo) \quad (13B)$$

$$(n_o - n_m)S_1 + (n_e - n_m)S_2 = D(oe) \quad (13C)$$

$$(n_e - n_m)S_1 + (n_e - n_m)S_2 = D(oo) = D_{e,m} \quad (13D)$$

The power D (oe) is provided by rays which are ordinary rays in the first lens and extraordinary rays in the second lens.

It is obvious that from equations 12 and e.g. 13B the shape factors $S_1$ and $S_2$ can be calculated for a desired, i.e. deliberately selectable power D (eo). From the set of equations 13 it is apparent that $D(eo) - D(oo) = D(ee) - D(oe)$. Furthermore, the powers D(eo) and D(oe) can be made equal; The lens is then trifocal with $S_1 = S_2 = S/2$.

The intensities associated with the individual powrs are given by:

$$I(oo) = (I/2)\cos^2\beta \quad (14A)$$

$$I(eo) = (I/2)\sin^2\beta \quad (14B)$$

$$I(oe) = (I/2)\sin^2\beta \quad (14C)$$

$$I(ee) = (I/2)\cos^2\beta \quad (14D)$$

where $\beta$ is the angle between the crystal optic axes of the two lens components, and I is the total intensity of the incident natural light (neglecting minor lens transmission losses). With respect to the four intensities I(oo) to I(oe) the same applies as mentioned above in connection with the power D(oe).

By way of example, it is assumed that a lens system according to FIG. 2 has to exhibit a minimum of 20 diopters and a maximum power of 24 diopters, respectively, when immersed in a medium of refractive index $n_m = 1.336$. If the lens is to be fabricated from polycarbonate, the required birefringence is approximately 0.05. If a slab of polycarbonate is stretched in order to exhibit the required adjusted birefringence, it will exhibit typically the indices $n_o = 1.583$ and $n_e = 1.633$ (the indices of refraction of different species of polycarbonate may differ). The shape factor S according to equation 11 is then approximately 81 m$^{-1}$. If the lens system according to FIG. 2 is composed of two lens components of shape factors $S_1 = 0.25$ S and $S_2 = 0.75$S, respectively, the lens system will provide the four powers: 20, 21, 23 and 24 diopters.- A lens system with e.g. the radii $R_1 = 18$ mm, $R_2 = 28.3$ mm and $R_3 = 39.3$ mm fabricated from the mentioned polycarbonate material will satisfy the mentioned requirements. Mention is made of the fact that one degree of freedom in the choice of lens radii exists.

If, by way of example, 30% of the incident intensity should show up in the smallest and largest power each, the angle $\beta$ between the crystal optic axes has to be chosen to be 39.2 degrees. Both intermediate powers will then carry 20% of the incident intensity.

It appears to be obvious how equations 13A to 13D and 14A to 14D have to be extended to describe the total eight powers and associated intensities available from a lens system consisting of three lenses according to FIG. 3.

A lens system according to FIG. 3 can provide five to eight different powers, depending on the choice of individual shape factors $S_1$, $S_2$ and $S_3$ of lenses 13,14 and 15, respectively. The following general rules can be established:

$$S_1 \neq S_2, S_1 + S_2 < S_3 \text{:octafocal}$$

$$S_1 \neq S_2, S_1 + S_2 = S_3 \text{:heptafocal}$$

$$S_1 = S_2, S_1 + S_2 < S_3 \text{:hexafocal}$$

$$S_1 = S_2 = S_3/2 = S/4 \text{:pentafocal}$$

The number of available powers can be reduced, if one of the angles between the crystal optic axes is made either 0 or 90 degrees; then, the system of FIG. 3 corresponds to that of FIG. 2.

By way of particular example, a lens system fabricated from stretched polycarbonate of indices $n_o = 1.583$ and $n_e = 1.633$ and exhibiting the three shape factors $S_1 = S_2 = 0.15$ S and $S_3 = 0.70$ S and the two angles $\beta_1 = 35$ degrees and $\beta_2 = 45$ degrees provides the following powers and associated intensities when immerset in a medium of $n_m = 1.336$.

20.0 diopters with 16.7% of the incoming intensity
20.6-"-16.4-"-
21.2-"-16.9-"-
22.8-"-16.9-"-
23.4-"-16.6-"-
24.0-"-16.7-"-

Such a lens system is feasible as an intraocular lens which would tolerate miscalculations of required viewing and reading powers.

It is considered obvious how the relations for lens systems incorporating still more lens components are to be established.

Although illustrative embodiments of the present invention have been described herein with reference to the accompanying drawings, it is to be understood that the invention is not limited to these precise embodiments, and that various other changes and modifications may be effected therein by one skilled in the art without departing from the scope or spirit of the invention.

I claim:

1. A multifocal lens system comprising at least one lens made of birefringent material, the birefringent material being a polymer which has been made birefringent by an orienting process including stretching of the polymer under defined conditions, the material exhibiting an ordinary refractive index $n_o$ and an extraordinary refractive index $n_e$ after the orienting process, characterized in that the birefringence of the birefringent material is adjusted by means of the orienting process that for the value of the birefringence an $\delta n = n_e - n_o$, one of a first equation $$\delta n = (n_o - n_m)\left(\frac{D_{max}}{D_{min}} - 1\right)$$

and a second equation $$\delta n = (n_o - n_m)\left(\frac{D_{min}}{D_{max}} - 1\right)$$

is satisfied, where $D_{max}$ and $D_{min}$ are two powers necessary for a specific optical application, the powers being measured for the lens system being immersed in a medium of refractive index $n_m$.

2. A multifocal lens system according to claim 1 wherein the birefringent lens is a bifocal single lens, which substantially exhibits the two powers $D_{max}$ and $D_{min}$.

3. A multifocal lens system according to claim 2 wherein the lens system is an ophthalmic lens system.

4. A multifocal lens system according to claim 2 wherein the lens system is an intraocular lens system.

5. A multifocal lens system according to claim 1 wherein adjacent lenses are attached together.

6. A multifocal lens system according to claim 1 wherein the lens system exhibits powers which are at least equal to $D_{min}$ and at most equal to $D_{max}$.

7. A multifocal lens system according to claim 1 wherein the lens system exhibits powers $D_{min}$ and $D_{max}$, wherein $D_{max}$ is provided by light rays which are ordinary rays in all birefringent lenses and wherein $D_{min}$ is provided by light rays which are extraordinary rays in all birefringent lenses.

8. A multifocal lens system according to claim 1 having at least two lenses wherein the number of selectable powers is substantially equivalent to one plus the number of lenses of the multifocal lens system, wherein $D_{min}$ and $D_{max}$ are selectable powers.

9. A multifocal lens system according to claim 1 wherein the lens system is an ophthalmic lens system.

10. A multifocal lens system according to claim 9 wherein the lens system is an intraocular lens.

11. A birefringent material suitable for manufacturing a bifocal birefringent lens, wherein the birefringent material is a polymer which is made birefringent by an orienting process including stretching of the polymer under defined conditions, the polymer exhibiting an ordinary refractive index $n_o$ and an extraordinary refractive index $n_e$ after the orienting process, wherein the birefringence of the birefringent material is adjusted by means of the orienting process that for the value of the birefringence $\delta n = n_e - n_o$, one of a first equation $$\delta n = (n_o - n_m)\left(\frac{D_{max}}{D_{min}} - 1\right)$$

and a second equation $$\delta n = (n_o - n_m)\left(\frac{D_{min}}{D_{max}} - 1\right)$$

is satisfied, where $D_{max}$ and $D_{min}$ are two powers necessary for a specific optical application, the powers being measured for the lens system being immersed in a medium of refractive index $n_m$.

12. A lens system having at least two lenses wherein each lens is composed of a material as defined by claim 11.

13. A lens system according to claim 12 wherein adjacent lenses are attached together.

14. A lens system according to claim 12 wherein all powers of the lens system exhibit values which are at least equal to $D_{min}$ and at most equal to $D_{max}$.

15. A lens system according to claim 12 wherein the lens system exhibits the powers $D_{min}$ and $D_{max}$, wherein $D_{max}$ is provided by light rays which are ordinary rays in all birefringent lenses and wherein $D_{min}$ is provided by light rays which are extraordinary rays in all birefringent lenses.

16. A lens system according to claim 12 having at least two lenses wherein the number of the selectable powers is substantially equivalent to one plus the number of lenses of the lens system, wherein $D_{min}$ and $D_{max}$ are selectable powers.

17. A lens system according to claim 12 wherein the lens system is an ophthalmic lens system.

18. A lens system according to claim 17 wherein the lens system is an intraocular lens system.

* * * * *

UNITED STATES PATENT AND TRADEMARK OFFICE
CERTIFICATE OF CORRECTION

PATENT NO. : 5,410,375
DATED : April 25, 1995
INVENTOR(S) : Werner J. Fiala

It is certified that error appears in the above-indentified patent and that said Letters Patent is hereby corrected as shown below:

Column 1, Line 64, delete "power" and insert --powers--.

Column 3, Line 49, after "associated", "lens surface is concave for incident light." should follow immediately thereafter as part of the same sentence.

Column 3, Line 50, after "light.", a new paragraph should begin with "If".

Column 8, Line 35, delete "16.6" and insert --16.4--;

Column 8, line 61, delete "an".

Signed and Sealed this

Fourth Day of July, 1995

Attest:

BRUCE LEHMAN

Attesting Officer

Commissioner of Patents and Trademarks